United States Patent [19]

Roy

[11] Patent Number: 5,087,436

[45] Date of Patent: Feb. 11, 1992

[54] RECOVERY OF COMMERCIALLY VALUABLE PRODUCTS FROM SCRAP TIRES

[75] Inventor: Christian Roy, Sillery, Canada

[73] Assignee: Universite Laval, Ste Foy, Canada

[21] Appl. No.: 553,569

[22] Filed: Jul. 17, 1990

Related U.S. Application Data

[63] Continuation-in-part of Ser. No. 372,568, Jun. 28, 1989.

[51] Int. Cl.$^5$ .............................................. C09C 1/48
[52] U.S. Cl. ..................................... 423/461; 423/445
[58] Field of Search ............... 423/450, 461, 445, 449; 524/495, 496; 201/2.5

[56] References Cited

U.S. PATENT DOCUMENTS

| | | | |
|---|---|---|---|
| 3,952,087 | 4/1976 | Antonsen et al. | 423/450 |
| 3,966,487 | 6/1976 | Crane et al. | 423/461 |
| 3,978,199 | 8/1976 | Maruhnic et al. | 423/449 |
| 4,002,587 | 1/1977 | Watanabe et al. | 423/449 |
| 4,250,145 | 2/1981 | Pobst, Jr. et al. | 423/450 |
| 4,250,158 | 2/1981 | Solbakken et al. | 201/2.5 |
| 4,284,616 | 8/1981 | Solbakken et al. | 423/449 |
| 4,740,270 | 4/1988 | Roy | 201/35 |
| 4,839,151 | 6/1989 | Apffel | 423/450 |

OTHER PUBLICATIONS

Data derived from: Kirk–Othmer: Encyclopedia of Chemical Technology: vol. 4: Third Edition, p. 658; vol. 10: Section: "Fillers"; vol. 20: Section: "Rubber Compounding".

Cabot Corporation Inc., Technical Service Report TG–76–1R#2: "Cabot Carbon Black Selection of Rubber Compounding".

Primary Examiner—Michael Lewis
Assistant Examiner—Stephen G. Kalinchak
Attorney, Agent, or Firm—Foley & Lardner

[57] ABSTRACT

Commercially valuable chemicals are extracted from tire-derived pyrolytic oils by subjecting the pyrolytic oils to a fractional distillation at a temperature of up to about 204° C. under atmospheric pressure to isolate at least one commercially valuable chemical selected from the group consisting of paraffins, naphthenes, olefins and aromatics. Particularly valuable chemicals which can be extracted from tire-derived pyrolytic oils are benene, toluene, xylene, styrene and limonene-dl. The distillation fraction boiling above 204° C. can be used as an extension oil in the manufacture of various rubber and plastic parts. Also disclosed is an improved process for producing carbon black by vacuum pyrolysis of used rubber tires.

4 Claims, 1 Drawing Sheet

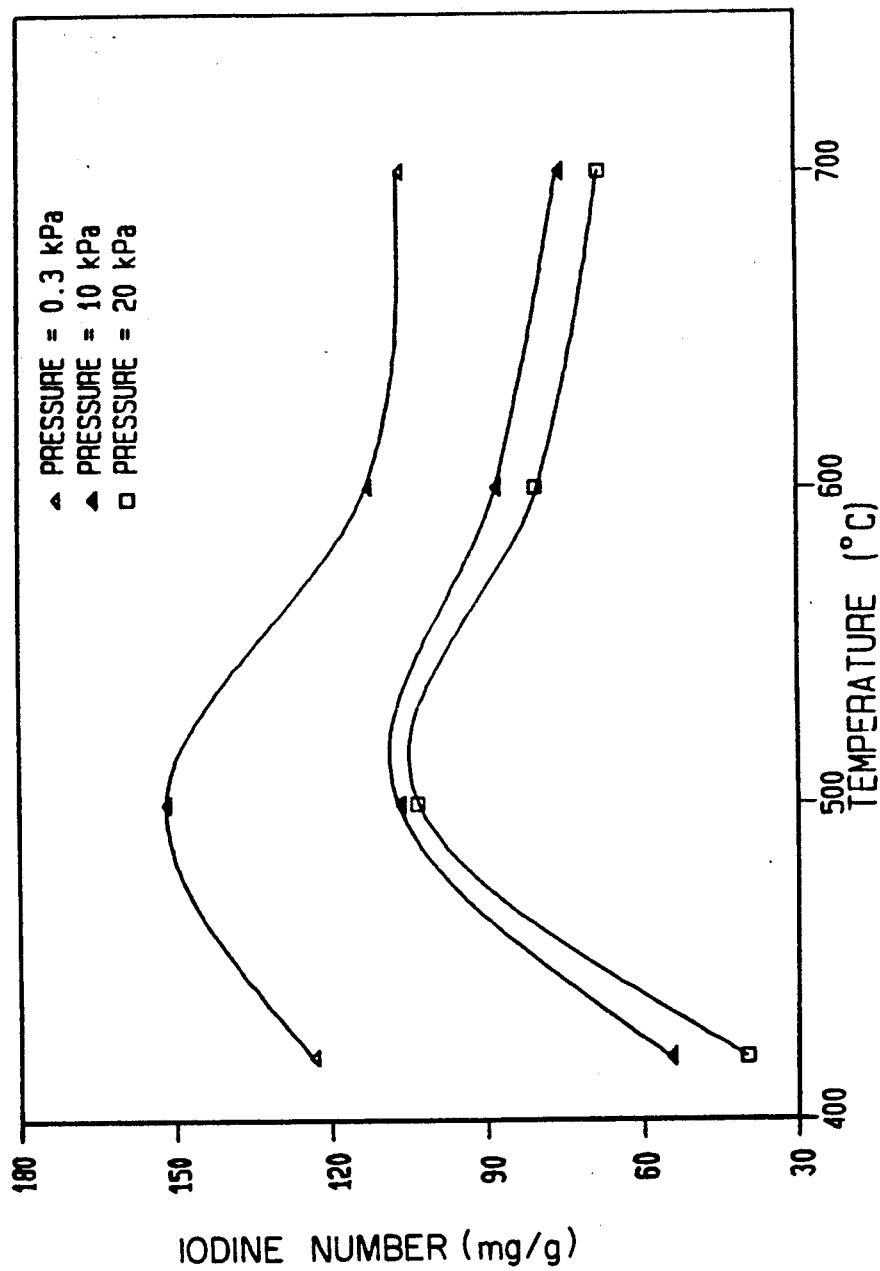

RECOVERY OF COMMERCIALLY VALUABLE PRODUCTS FROM SCRAP TIRES

CROSS-REFERENCE TO RELATED APPLICATIONS

This application is a continuation-in-part of U.S. patent application Ser. No. 372,568, filed on June 28, 1989 now pending.

BACKGROUND OF THE INVENTION

The present invention relates to improvements in the field of tire recycling. More particularly, the invention is directed to the recovery of commercially valuable products from used rubber tires.

Tire recycling has become a necessity because of the accumulation of large quantities of scrap tires which represents a major environmental problem. Each year, about 24 million used rubber tires are disposed of in Canada and about 250 million in the United States. While some of these tires are recapped or ground up for special uses, most are simply dumped in rural farm land or in landfill sights. When buried in landfills they eventually float to the surface, and when piled the non-biodegradable rubber will cause serious damage if ignited by lightning or vandals.

On the other hand, used rubber tires represent a source of energy and raw products for the production of rubber parts. By thermal decomposition of rubber, it is possible to recover to a certain extent the initial ingredients which constitute a tire. To this end, Applicant has already proposed in U.S. Pat. No. 4,740,270 a process for the treatment of used rubber tires by vacuum pyrolysis in a reactor to produce liquid and gaseous hydrocarbons and a solid carbonaceous material. According to this process, the pyrolysis of the tires is carried out at a temperature in the range of about 360° C. to about 415° C., under a subatmospheric pressure of less than about 35 mm Hg and such that gases and vapors produced in the reactor have a residence time of the order of a few seconds. As a result, pyrolytic oils are obtained in substantially maximum yield. Typically, about 60 weight % hydrocarbon oils, about 38 weight % solid carbonaceous material and about 2 weight % gaseous hydrocarbons can be produced by such a process. As indicated in Applicant's aforementioned patent, the hydrocarbon oils produced have a calorific value of about 10,200 kcal kg$^{-1}$ and are thus suitable for use as heating fuel. However, it would be desirable to increase the value of these pyrolytic oils with a view to obtaining commercially valuable chemicals.

SUMMARY OF THE INVENTION

It is therefore an object of the present invention to extract commercially valuable chemicals from tire-derived pyrolytic oils.

It is another object of the invention to recover other commercially valuable products from used rubber tires.

According to one aspect of the invention, there is provided a method of extracting commercially valuable chemicals from tire-derived pyrolytic oils, which comprises subjecting the pyrolytic oils to a fractional distillation at a temperature of up to about 204° C. under atmospheric pressure to isolate at least one commercially valuable chemical selected from the group consisting of paraffins, naphthenes, olefins and aromatics.

Preferably, the method of the invention involves two fractional distillations and thus comprises the steps of:

a) subjecting the pyrolytic oils to a fractional distillation at a temperature of up to about 204° C. under atmospheric pressure;

b) recovering a fraction boiling in the range of about 43° C. to about 204° C.; and c) subjecting the fraction to a further fractional distillation to isolate at least one commercially valuable chemical selected from the group consisting of paraffins, naphthenes, olefins and aromatics.

Applicant has found quite unexpectedly that the distillation fraction boiling below 204° C. obtained by fractional distillation of tire-derived pyrolytic oils contains commercially valuable chemicals. The PONA analysis of such a fraction which constitutes about 27 weight % of the pyrolytic oils gave about 25 weight % paraffins, about 7 weight % naphthenes, about 43 weight % olefins and about 25 weight % aromatics. It has a calorific value of about 43,700 Jg$^{-1}$.

Particularly interesting compounds identified in the above distillation fraction are benzene (b.p. 80.1° C.), toluene (b.p. 110.6° C.), o-xylene (b.p. 144.4° C.), m-xylene (b.p. 139.1° C.), p-xylene (b.p. 138.3° C.) and styrene (b.p. 145.2° C.). These compounds can be used as solvents and petrochemical feedstock in the synthesis of various polymers. For example, styrene is mainly used in the production of plastics, rubber and resins. Xylene is particularly useful in the production of polyester fibers; it is also used as solvent and starting material in the production of benzoic and isophthalic acids. Toluene is also used for the production of benzoic acid.

Another compound of interest identified in the fraction boiling below 204° C. is limonene-dl (b.p. 178° C.) which constitutes the major component of the fraction. The presence of limonene-dl is totally unexpected since this compound is a terpene which is usually derived from essential oils such as lemon and orange oils. It is mainly used as a flavoring agent in the food and fragrance industries.

Thus, by carrying out the fractional distillation of the pyrolytic oils to recover a fraction boiling in the range of about 70° C. to about 204° C., it is possible to concentrate in such a fraction the above commercially valuable chemicals. This distillation fraction can typically contain about 3 weight % benzene, about 8 weight % toluene, about 7 weight % xylene, about 6 weight % styrene and about 17 weight % limonene-dl.

The present invention therefore provides, in another aspect thereof, a distillation fraction boiling in the range of about 43° C. to about 204° C., preferably from about 70° C. to about 204° C., under atmospheric pressure and obtained by fractional distillation of tire-derived pyrolytic oils.

According to a further aspect of the invention, there is also provided a method of extracting limonene-dl from a distillation fraction boiling in the range of about 43° C. to about 204° C., preferably from about 70° C. to about 204° C., under atmospheric pressure and obtained by fractional distillation of tire-derived pyrolytic oils, which comprises subjecting the fraction to a fractional distillation at a temperature of about 178° C. under atmospheric pressure to isolate limonene-dl.

The tire-derived pyrolytic oils used in accordance with the invention therefore constitute a source of commercially valuable chemicals and thus enable the vacuum pyrolysis of used rubber tires to become a commercially attractive solution to the problems created by the accumulation of large quantities of scrap tires.

Applicant has further found quite unexpectedly that the heavy oil fraction which is obtained as a by-product in the above fractional distillation of tire-derived pyrolytic oils, that is, the distillation fraction boiling above about 204° C. under atmospheric pressure, can be used as an extension oil in the manufacture of various rubber and plastic parts. Thus, such a heavy oil fraction also represents a commercially valuable product.

According to yet another aspect of the invention, there is therefore provided an extension oil comprising a distillation fraction boiling above about 204° C. under atmospheric pressure and obtained by fractional distillation of tire-derived pyrolityc oils. Preferably, such an extension oil comprises the distillation fraction boiling in the range of about 350° to about 575° C.

The extension oil obtained in accordance with the invention advantageously compares with commercially available extension oils, such as SUNDEX (trade mark), as may be seen from the following Table 1:

TABLE 1

| PHYSICAL PROPERTIES | SUNDEX Extension Oil | | | Extension Oil of Invention |
|---|---|---|---|---|
| | 750 T | 740 T | 8125 | |
| Viscosity, SUS/100° C. | 450 | 100 | 7000 | 330 |
| Viscosity, SUS/210° C. | 50.2 | 37.3 | 123 | 45.5 |
| °API, 60° F. | 16.0 | 19.5 | 10.0 | 15.9 |
| Specific Gravity, 60° F. | 0.9593 | 0.9371 | 1.000 | 0.9595 |
| Viscosity-Constant | | | | |
| Gravity | 0.920 | 0.933 | 0.946 | 0.952 |
| Density (lb./gal.) | 7.99 | 7.80 | 8.33 | 8.01 |
| Molecular Weight | 347 | 287 | 395 | 320 |
| Pour Point (°F.) | +35 | +35 | +55 | +48 |
| Volatility (wt. %, 225° F.) | 0.3 | 2.7 | 0.5 | 0.9 |
| Flash Point (°F.) | 400 | 340 | 445 | 390 |
| Refraction Index | 1.5382 | 1.5306 | 1.5725 | 1.5258 |
| Aniline Point (°F.) | 121 | 104 | 95 | 91 |
| Aromatics Content (wt. %) | 71.7 | 68.4 | 84.4 | 87.2 |

The solid carbonaceous material which is obtained as a by-product in the vacuum pyrolysis of used rubber tires contains a significant amount of carbon blacks. Such carbon blacks, however, have a low specific surface area which renders them unsuitable for most applications where high-grade carbon blacks are required.

The iodine adsorption number of a carbon black is a direct indication of its specific surface area. This particular property is considered to be one of the most important means by which a carbon black can be evaluated. In the case of carbon blacks obtained by vacuum pyrolysis of used rubber tires at temperatures in the range of 360°–415° C. under an absolute pressure of less than 5 kPa, the iodine adsorption number is generally below 75 mg/g.

Applicant has now found quite unexpectedly that by increasing the reactor bed temperature from 415° C. to a temperature in the range of about 490°–510° C., while maintaining an absolute pressure of less than about 5 kPa, the iodine adsorption number of the carbon black produced can be significantly increased, to about 130°–150 mg/g. However, upon increasing the temperature above 510° C., the residual carbonaceous solids are subjected to a series of complex changes which result in a drastic decrease of the iodine index.

According to still a further aspect of the invention, there is thus provided a process for producing carbon black by vacuum pyrolysis of used rubber tires, which comprises pyrolysing used rubber tire material at a temperature in the range of about 490° C. to about 510° C. under an absolute pressure of less than about 5 kPa, and recovering a solid carbonaceous material containing carbon black having an iodine adsorption number of about 130 to about 150 mg/g.

In a preferred embodiment, the vacuum pyrolysis is carried out at a temperature of about 500° C. under an absolute pressure of about 0.3 kPa so as to produce a carbon black having an iodine adsorption number of about 150 mg/g.

The general properties of the carbon black produced in accordance with the invention are summarized in the following Table 2:

TABLE 2

| Iodine index (mg/g) | 130–150 |
|---|---|
| DBP adsorption (ml/100 g) | 80–100 |
| Heat loss at 105° C. (%) | 0.3–1.4 |
| Tint strength | 55–63 |
| Ash (%) | 15–17 |
| Volatile Matter (%) | 2–5 |
| S (%) | 2.5–3.0 |

The tire-derived carbon black of the invention can be used as filler for rubber goods such as sidewalls for vehicle tires, footwears, rubber sheets, conveyer belts, dock fenders, bicycle tires, etc. Another application of such a carbon black is as a raw material for activated carbon.

BRIEF DESCRIPTION OF THE DRAWINGS

Further features and advantages of the invention will become more readily apparent from the following non-limiting examples and the accompanying drawings, in which:

FIG. 1 is a plot of the iodine adsorption number of carbon blacks produced by vacuum pyrolysis of used rubber tires, as a function of temperature for various pressures.

EXAMPLE 1

Used rubber tires in the form of cuttings were treated by vacuum pyrolysis in accordance with Example No. 5 of U.S. Pat. No. 4,740,270 to produce 61.2 weight % hydrocarbon oils, 36.6 weight % char and 2.2 weight % gases. These pyrolytic oils were then subjected to a fractional distillation by slowly heating the oils up to a temperature of about 204° C. under atmospheric pressure and recovering a fraction boiling in the range of about 43° C. to about 204° C. This fraction which constituted about 26.8 weight % of the pyrolytic oils was subjected to a further fractional distillation to isolate the major components thereof. The results are reported in the following Table 3:

TABLE 3

| Components | Weight % (*) |
|---|---|
| Methylpentene | 1.44 |
| Dimethylpentane | 1.04 |
| Benzene | 2.54 |
| 2,4,4-Trimethyl-1-pentene | 1.43 |
| Dimethylcyclopentadiene | 1.58 |

TABLE 3-continued

| Components | Weight % (*) |
| --- | --- |
| Toluene | 6.95 |
| Cyclopentanone | 1.00 |
| 4-Vinyl-1-cyclohexene | 1.66 |
| o-Xylene | 0.91 |
| m-Xylene | 2.43 |
| p-Xylene | 2.78 |
| Styrene | 5.44 |
| a-Methylstyrene | 1.23 |
| Limonene-dl | 14.92 |

(*) based on the total mass of the fraction.

As it is apparent from Table 3, the compounds of interest, namely benzene, toluene, xylene, styrene and limonene-dl, are present in the fraction boiling in the range of 43°-204° C., in relatively important quantities.

EXAMPLE 2

The procedure of Example 1 was repeated, except that a fraction boiling in the range of about 70° C. to about 204° C. was recovered. This fraction was subjected to a further fractional distillation to isolate benzene, toluene, xylene, styrene and limonene-dl. The results are reported in the following Table 4:

TABLE 4

| Components | Weight % (*) |
| --- | --- |
| Benzene | 2.8 |
| Toluene | 7.7 |
| o-Xylene | 1.0 |
| m-Xylene | 2.7 |
| p-Xylene | 3.1 |
| Styrene | 6.1 |
| Limonene-dl | 16.6 |

(*) based on the total mass of the fraction.

As it is apparent from Table 4, by carrying out the fractional distillation of the pyrolytic oils to recover a fraction boiling in the range of 70°-204° C., it is possible to concentrate in such a fraction the above commercially valuable chemicals.

EXAMPLE 3

Used rubber tires in the form of cuttings were treated by vacuum pyrolysis in accordance with Example 5 of U.S. Pat. No. 4,740,270, with the exception that the reactor bed temperature was increased from 420° C. to 700° C. and the pressure conditions were varied. The iodine adsorption numbers of the carbon blacks produced at varying temperatures and pressures were measured. The results of iodine adsorption number measurements as a function of the operating conditions used are reported in the following Table 5:

TABLE 5

| EXPERIMENT No. | TEMPERATURE (°C.) | PRESSURE (kPa) | IODINE ADSORPTION NUMBER (mg g$^{-1}$) |
| --- | --- | --- | --- |
| 1 | 350 | 0.3 | — |
| 2 | 420 | " | 124 |
| 3 | 500 | " | 151 |
| 4 | 600 | " | 113 |
| 5 | 700 | " | 105 |
| 6 | 700 | " | 107 |
| 7 | 420 | 10 | 59 |
| 8 | 550 | " | 110 |
| 9 | 550 | " | 105 |
| 10 | 700 | " | 62 |
| 11 | 420 | 20 | 55 |
| 12 | 700 | " | 62 |
| 13 | 420 | 10 | 55 |
| 14 | 500 | " | 107 |
| 15 | 600 | " | 80 |
| 16 | 700 | " | 76 |
| 17 | 420 | 20 | 40 |
| 18 | 500 | " | 103 |
| 19 | 600 | " | 88 |
| 20 | 700 | " | 68 |

The variation of the iodine adsorption number as a function of the reactor bed temperature, for various reactor pressures, is plotted in FIG. 1. As may be seen, the curves in FIG. 1 indicate a strong dependency of the specific surface area as a function of pyrolysis temperature. For all operating pressures, the curves look similar with a bell shape centered around 500° C.

The best quality carbon black is produced at a final bed temperature of 500° C. and an operating pressure of 0.3 kPa absolute.

The variation of the specific surface area with temperature can be explained as follows. Upon increasing the reactor bed temperature from 420° to 500° C., the excess rubber organic ingredients from the pores and the surface are pulled out and removed. This results, at the beginning, in a sharp increase in the iodine adsorption number. However, upon increasing the temperature above 500° C., the residual carbonaceous solids are subjected to a series of complex changes. These changes are the main sources for the drastic decrease in iodine index.

The changes in residual solid properties take place by a series of consecutive and parallel reactions, involving both the solid residue and evolved hydrocarbons. One of these modifications involves the deposition of pyrolytic carbon in the pores and on the surface of the carbon black. Other modifications involve the elimination and screening of the surface functional groups. In the former case, pyrolytic carbon is formed through the pyrolysis of generated hydrocarbon vapors and gases. However, in the latter case, the surface functional groups are screened by pyrolytic carbon deposition, and eliminated by the degassing of carbon-oxygen and carbon-hydrogen complexes.

Some of the main characteristic of the carbon black produced by vacuum pyrolysis of used rubber tires at 500° C. and 0.3 kPa are summarized in the following Table 6, and compared with the properties of two commercially available carbon black, N-234 and N-330:

TABLE 6

| PHYSICOCHEMICAL PROPERTIES | N-234 | N-330 | CARBON BLACK PRODUCED BY PYROLYSIS AT 500° C. and 0.3 kPa |
| --- | --- | --- | --- |
| Surface Area | | | |
| Iodine index (mg g$^{-1}$) | 112.7 | 80.5 | 151.5 |
| Proximate Analysis | | | |
| Volatile Content (wt. %) | 4.2 | 3.3 | 2.8 |
| Loss at 105° C. (wt. %) | 3.2 | 2.5 | 0.2 |
| Fixed Carbon (wt. %) | 95.2 | 96.4 | 85.8 |
| Ash Content (wt. %) | 0.6 | 0.3 | 11.4 |
| Wettability | Hydrophilic | Hydrophilic | Hydrophobic |

TABLE 6-continued

| PHYSICOCHEMICAL PROPERTIES | N-234 | N-330 | CARBON BLACK PRODUCED BY PYROLYSIS AT 500° C. and 0.3 kPa |
|---|---|---|---|
| Elemental Analysis | | | |
| Carbon (wt. %) | 94.81 | 96.00 | 85.17 |
| Hydrogen (wt. %) | 0.84 | 0.66 | 0.74 |
| Nitrogen (wt. %) | 0.77 | 0.60 | 0.76 |
| Oxygen (wt. %) | 2.98 | 1.98 | 1.95 |
| pH | 4.2 | 7.3 | 8.7 |

As may be seen from Table 6, the carbon black obtained by vacuum pyrolysis of used rubber tires has an iodine adsorption number superior to those of the standard reference blacks N-234 and N-330. The tire-derived carbon black is basic as evidenced by the pH of 8.7, whereas the commercial black N-234 is acidic and N-330 is almost neutral.

However, the significant difference between the tire-derived carbon black and the commercial carbon blacks is their high inorganic material or ash content. The inorganic content of tire-derived blacks is generally higher than 10%.

In all cases, carbon black produced by rubber pyrolysis is distinctly different from commercial blacks. This difference would originate mainly from the interactions of the solid residue with the products of hydrocarbon pyrolysis reactions. The deviation from the parent properties would originate partly from the surface thermal treatment of carbon black during pyrolysis process.

I claim:

1. A carbon black produced by vacuum pyrolysis of used rubber tires at a temperature in the range of about 490° C. to about 510° C. under an absolute pressure of less than about 5 kPa, and having an iodine adsorption number of about 130 to about 150 mg/g, a DBP adsorption of 80 to 100 ml/100 g and a tint strength number of 55 to 63.

2. A carbon black produced by vacuum pyrolysis of used rubber tires at a temperature of about 500° C. under an absolute pressure of about 0.3 kPa, and having an iodine adsorption number of about 150 mg/g, a DBP adsorption of 80 to 100 ml/100 g and a tint strength number of 55 to 63.

3. A carbon black as claimed in claim 1, having a hydrophobic character and an ash content of from above 10 to 17 wt. %.

4. A carbon black as claimed in claim 2, having a hydrophobic character and an ash content of 11.4 wt. %.

* * * * *